United States Patent
Nguyen et al.

(10) Patent No.: US 9,636,132 B2
(45) Date of Patent: May 2, 2017

(54) TUMOR DEBULKER

(71) Applicant: MEDTRONIC-XOMED, INC., Jacksonville, FL (US)

(72) Inventors: Thoai Nguyen, Jacksonville, FL (US); Phillip J. Berman, Jacksonville, FL (US); Dana A. Oliver, Jacksonville, FL (US); Louis M. Shadeck, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 162 days.

(21) Appl. No.: 14/479,714

(22) Filed: Sep. 8, 2014

(65) Prior Publication Data

US 2016/0066942 A1 Mar. 10, 2016

(51) Int. Cl.
*A61B 17/12* (2006.01)
*A61B 17/32* (2006.01)
*A61B 17/00* (2006.01)

(52) U.S. Cl.
CPC ........... *A61B 17/32002* (2013.01); *A61B 2017/00477* (2013.01); *A61B 2017/00526* (2013.01); *A61B 2017/00845* (2013.01); *A61B 2017/320024* (2013.01); *A61B 2017/320032* (2013.01); *A61B 2217/005* (2013.01); *A61B 2217/007* (2013.01)

(58) Field of Classification Search
CPC .. A61B 17/32002; A61B 2017/320024; A61B 2017/00845; A61B 2017/00477; A61B 2217/007; A61B 2217/005; A61B 2017/320032
See application file for complete search history.

(56) References Cited

U.S. PATENT DOCUMENTS

| | | | |
|---|---|---|---|
| 4,167,943 A | | 9/1979 | Banko |
| 4,274,414 A | * | 6/1981 | Johnson ........... A61B 17/32002 606/170 |
| 4,598,710 A | † | 7/1986 | Kleinberg |
| 4,834,729 A | | 5/1989 | Sjostrom |
| 4,850,354 A | | 7/1989 | McGurk-Burleson et al. |
| RE33,258 E | | 7/1990 | Onik et al. |

(Continued)

FOREIGN PATENT DOCUMENTS

WO 2008124650 A1 10/2008

OTHER PUBLICATIONS

International Search Report and Written Opinion for Application No. PCT/US2015/48015, mailed Jan. 18, 2016, 15 pages.

(Continued)

*Primary Examiner* — Julian W Woo
(74) *Attorney, Agent, or Firm* — Dicke, Billig & Czaja, PLLC

(57) ABSTRACT

A cutting device for use with a powered surgical tool includes an outer blade and an inner blade. The outer blade includes a tubular body, an end cap, and a cutting window defined by a beveled edge on the tubular body and the end cap. The inner blade includes a cutting tip. The inner blade co-axially disposed within the outer blade such that the cutting tip is rotatably exposed at the cutting window. The cutting tip has castellations extending toward the end cap of the outer blade and opposing teeth extending radially toward one another across an opening of the cutting tip.

16 Claims, 11 Drawing Sheets

(56) References Cited

U.S. PATENT DOCUMENTS

| | | | |
|---|---|---|---|
| 4,983,179 A | | 1/1991 | Sjostrom |
| 4,986,827 A | | 1/1991 | Akkas et al. |
| 5,007,917 A | * | 4/1991 | Evans ............... A61B 17/32002 604/22 |
| 5,275,609 A | | 1/1994 | Pingleton et al. |
| 5,376,078 A | | 12/1994 | Dinger |
| 5,409,013 A | | 4/1995 | Clement |
| 5,601,583 A | | 2/1997 | Donahue et al. |
| 5,620,447 A | | 4/1997 | Smith et al. |
| 5,643,304 A | | 7/1997 | Schechter et al. |
| 5,669,876 A | | 9/1997 | Schechter et al. |
| 5,685,840 A | | 11/1997 | Schechter et al. |
| 5,709,698 A | | 1/1998 | Adams et al. |
| 5,782,795 A | | 7/1998 | Bays |
| 5,863,294 A | * | 1/1999 | Alden ............... A61B 17/32002 606/167 |
| 5,964,777 A | | 10/1999 | Drucker |
| 6,183,433 B1 | | 2/2001 | Bays |
| 6,217,598 B1 | | 4/2001 | Berman et al. |
| 6,620,180 B1 | | 9/2003 | Bays et al. |
| 6,638,289 B1 | | 10/2003 | Johnson et al. |
| 7,674,263 B2 | * | 3/2010 | Ryan ................... A61B 18/148 606/180 |
| 7,803,170 B2 | * | 9/2010 | Mitusina .......... A61B 17/32002 606/171 |
| 8,070,765 B2 | | 12/2011 | Oliver et al. |
| 8,202,288 B2 | | 6/2012 | Adams et al. |
| 8,409,235 B2 | | 4/2013 | Rubin |
| 8,414,606 B2 | * | 4/2013 | Shadeck .......... A61B 17/32002 606/170 |
| 9,486,232 B2 | * | 11/2016 | Heisler ............ A61B 17/32002 |
| 2005/0159767 A1 | | 7/2005 | Adams et al. |
| 2006/0200123 A1 | | 9/2006 | Ryan |
| 2007/0149975 A1 | | 6/2007 | Oliver et al. |
| 2007/0219549 A1 | | 9/2007 | Marshall et al. |
| 2007/0282361 A1 | | 12/2007 | Da Rold et al. |
| 2008/0200941 A1 | | 8/2008 | Mitusina |
| 2009/0270894 A1 | | 10/2009 | Rubin et al. |
| 2010/0152761 A1 | | 6/2010 | Mark |
| 2010/0191266 A1 | | 7/2010 | Oliver et al. |
| 2010/0298763 A1 | | 11/2010 | Adams et al. |
| 2012/0109172 A1 | | 5/2012 | Schmitz et al. |
| 2012/0157879 A1 | | 6/2012 | Mark et al. |
| 2012/0191117 A1 | | 7/2012 | Palmer et al. |
| 2013/0012972 A1 | | 1/2013 | Norman et al. |
| 2014/0303551 A1 | | 10/2014 | Germain et al. |

OTHER PUBLICATIONS

International Search Report and Written Opinion for Application No. PCT/US2015/47724, mailed Dec. 21, 2015, 15 pages.

\* cited by examiner
† cited by third party

TUMOR DEBULKER

CROSS-REFERENCE TO RELATED APPLICATIONS

This Utility Patent Application is related to concurrently filed Utility patent application Ser. No. 14/479,729, entitled METHOD FOR RESECTION OF TUMORS AND TISSUES and Utility patent application Ser. No. 14/479,720, entitled TUMOR MARGIN DEVICE.

BACKGROUND

The present disclosure relates to a method and instrument for debulking or reducing a large tissue volume such as a cyst or tumor. More particularly, it relates to surgical systems, instruments, and methods useful in reducing and removing tumors and fibrous tissues. The tissue often contains high collagen content and is a form of connective tissue. In terms of tumors arising from high collagen content tissues, the tumors may replicate the properties of the tissues and therefore present a challenge to resection.

Use of such surgical cutting instruments generally entails delivering a cutting window/cutting tip of a cutting implement to the target site and positioning the cutting window such that the cutting tip is exposed to the desired tissue. It is desirable to remove the center or bulk of the target tissue as quickly as possible. In this regard, a variety of surgical instruments, such as a cavitational ultrasonic surgical aspirator (CUSA) or a surgical laser knife, are commonly used.

A debulker is a type of microdebrider blade. A debulker mates with a surgical handpiece that provides irrigation fluid, suction, controlled torque to the inner blade member, and a mechanical interface to hold and position the debulker blade. Irrigation can be forced between the inner blade member and the outer blade driving the flow from a proximal end connected to the handpiece to the distal cutting end. The microdebrider blades often tear off chunks of tissue. When the blade resects the tissue a mixture of irrigant and resected tissue is drawn down the lumen of the inner blade member via suction and travels from the distal end to the proximal end to then exit through the handpiece.

In light of the above, a need exists for surgical systems and methods for quickly reducing or removing tumors and/or fibroid tissue.

SUMMARY

Some aspects in accordance with principles of the present disclosure related to a cutting device for use with a powered surgical tool. The cutting device includes an outer blade and an inner blade. The outer blade includes a tubular body, an end cap, and a cutting window defined by a beveled edge on the tubular body and the end cap. The inner blade includes a cutting tip. The inner blade co-axially disposed within the outer blade such that the cutting tip is rotatably exposed at the cutting window. The cutting tip has castellations extending toward the end cap of the outer blade and opposing teeth extending radially toward one another across an opening of the cutting tip.

Other aspects in accordance with principles of the present disclosure relate to a cutting device for use with a powered surgical tool. The cutting device includes an outer blade and an inner blade. The outer blade has a distal end having an end cap. The end cap is planar and perpendicular to cylindrical sides of the outer blade. A distal cutting window is formed in the end cap and the cylindrical sides. The distal cutting window is defined by edges having protrusions and window teeth. The inner blade has a distal portion including a cutting tip. The cutting tip includes teeth configured in pairs that extend radially toward one another across an opening. The inner blade is disposed coaxially within the outer blade along a longitudinal axis with the cutting tip aligned within the cutting window. The window teeth of the cutting window are longitudinally offset from the teeth of the cutting tip.

Other aspects in accordance with principles of the present disclosure relate to a method of manufacturing a surgical cutting device. The method includes fabricating an inner blade, fabricating an outer blade, applying a lubricating coating to an outer surface of the inner blade, and assembling the inner blade co-axially within the outer blade. Fabricating the inner blade includes selecting a non-tubular material member having a mass and selectively removing a majority of the mass of the non-tubular material member to form a tubular shaped distal portion having a cutting tip, wherein the distal portion has a first outer diameter. The distal portion is assembled to an end of a tubular main portion. The tubular main portion has a second outer diameter smaller than the first outer diameter of the distal portion. Fabricating the outer blade includes forming a tubular member with an end cap at the distal end of the tubular member. The tubular member has tubular side walls extending along an axis. An interior surface of the end cap is perpendicular to the tubular side walls. An interior surface of the tubular side walls intersects squarely with the interior surface of the end cap to form a right angled perimeter. The end cap and the tubular side walls at the distal end are selectively removed to form a cutting window. The lubricating coating is applied to an outer surface of the inner blade and the inner blade co-axially assembled within the outer blade with the cutting tip rotatably aligned within the cutting window.

DETAILED DESCRIPTION

Surgical instruments embodying principles of the present disclosure can be employed in various types of surgery including, but not limited to, neurosurgery or spinal surgery on the dura or spinal column. Surgical instruments according to aspects of the present disclosure can resect a wide range of tumors including very fibrous meningioma as part of a surgery.

Figure 1:
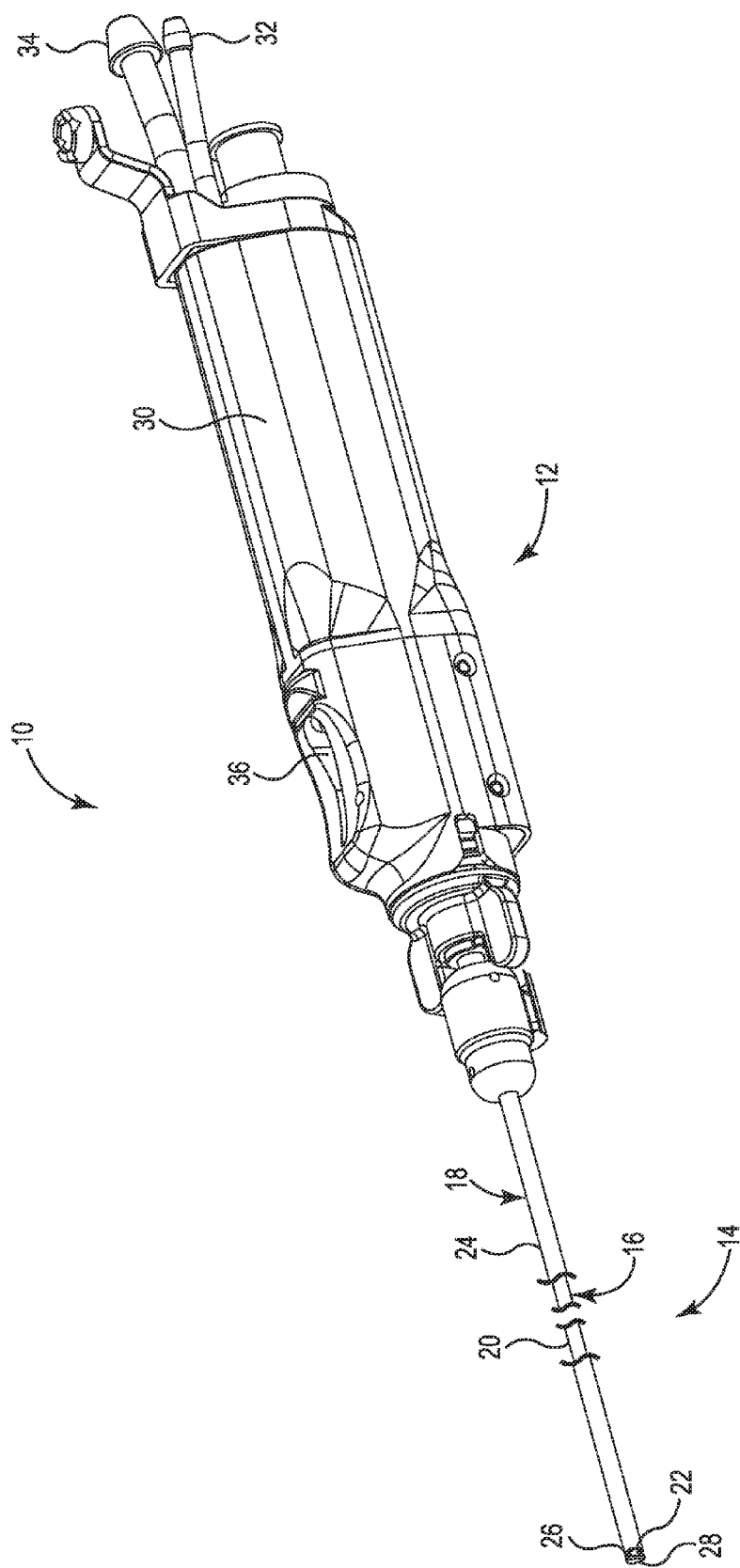
FIG. 1 is a perspective view of a surgical cutting instrument for surgically reducing or removing a tumor or fibrous tissue in accordance with principles of the present disclosure.

A surgical cutting instrument 10 in accordance with aspects of the present disclosure is shown in FIG. 1. The cutting instrument 10 includes a proximal handpiece 12 and a cutting implement 14 extending distally from the handpiece 12. The cutting instrument 10 includes an inner blade assembly 16 and an outer blade assembly 18. The inner blade assembly 16 includes an inner blade 20 which has a cutting tip 22. The outer blade assembly 18 includes an outer blade 24 which has a cutting window 26. The inner blade 20 is co-axially disposed within the outer blade 24 such that the cutting tip 22 is exposed at the cutting window 26 at the distal end 28 of the cutting implement 14. Details on the various components are provided below.

The handpiece 12 includes a housing 30 that contains a motor (not shown) for driving the rotational movement of the inner blade assembly 16. The handpiece 12 receives proximal ends of the inner and outer blade assemblies 16, 18 for fluidly connecting internal irrigation and aspiration paths (each not shown) with an irrigation port 32 and an aspiration port 34, respectively, assembled to the housing 30. Regardless, the irrigation path is formed within the housing 30 extending from the irrigation port 32, through the outer blade assembly 18 to the cutting window 26. The irrigation port 32, in turn, is adapted for fluid connection to tubing (not shown) that is otherwise connected to a fluid source (not shown). Similarly, the aspiration port 34 is assembly to the housing in fluid communication with the aspiration path formed within the housing 30 extending from the aspiration port 34, through the inner blade assembly 16 to the cutting tip 22. The aspiration port 34, in turn, is adapted for fluid connection to tubing (not shown) that is otherwise connected to a vacuum source (not shown) for applying a vacuum to the aspiration path, and thus to the inner blade 20. Additional control of the negative pressure supplied to the cutting tip 22 is provided by the aspiration control hole 36 on the handpiece 12.

Figure 2:
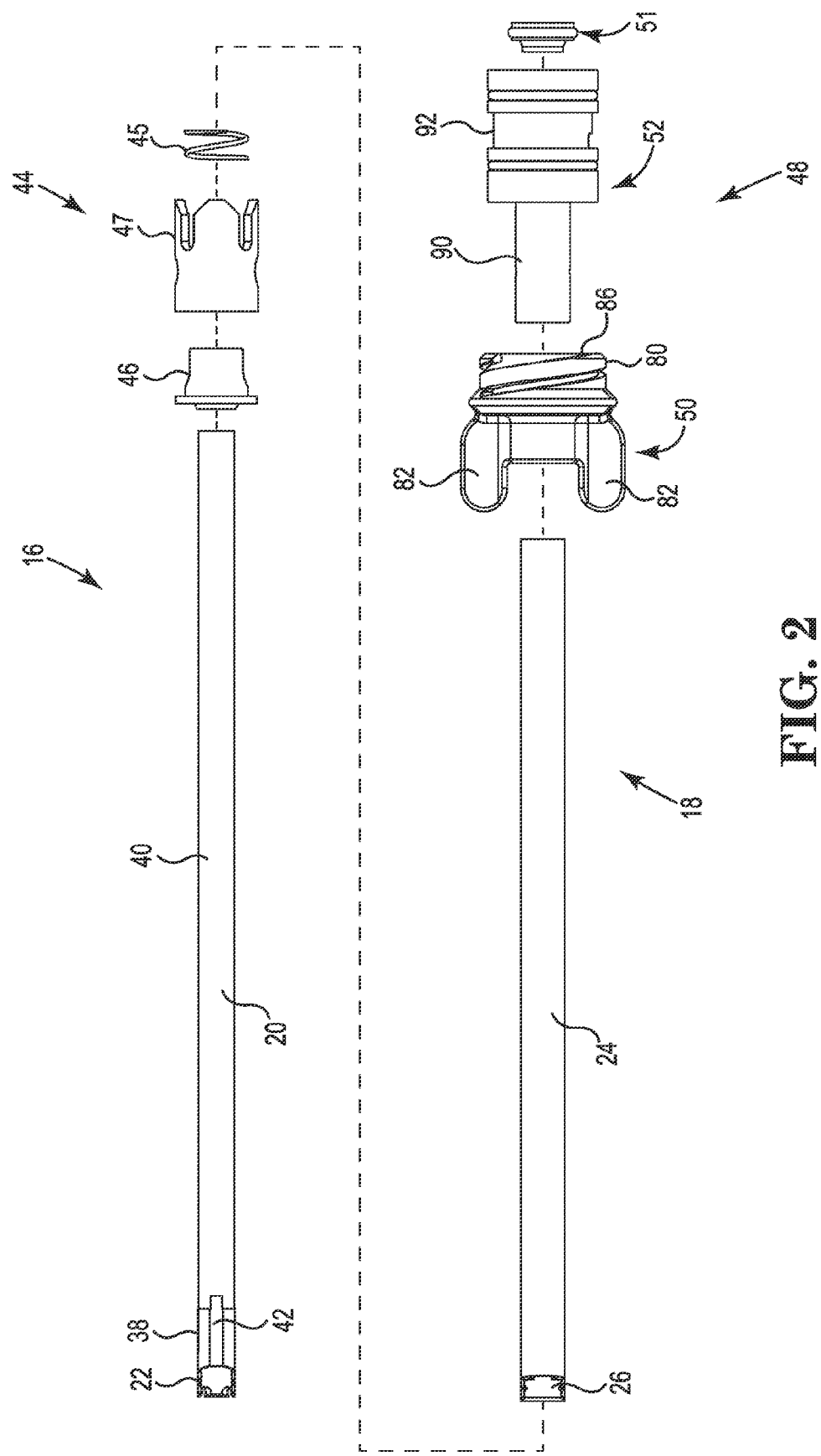
FIG. 2 is an exploded view of a cutting implement of a surgical cutting instrument of FIG. 1.

With the above general construction of the cutting instrument 10 in mind, features associated with the cutting implement 14 in accordance with aspects of the present disclosure are shown in greater detail in FIG. 2. The cutting implement 14 includes the inner blade assembly 16 having the inner blade 20 and the outer blade assembly 18 having the outer blade 24. In general terms and with additional reference to FIG. 3A, the inner blade 20 is rotatably received within the outer blade 24, with the other components of the inner and outer blade assemblies 16, 18 effectuating connection to the handpiece 12.

Figure 3A:
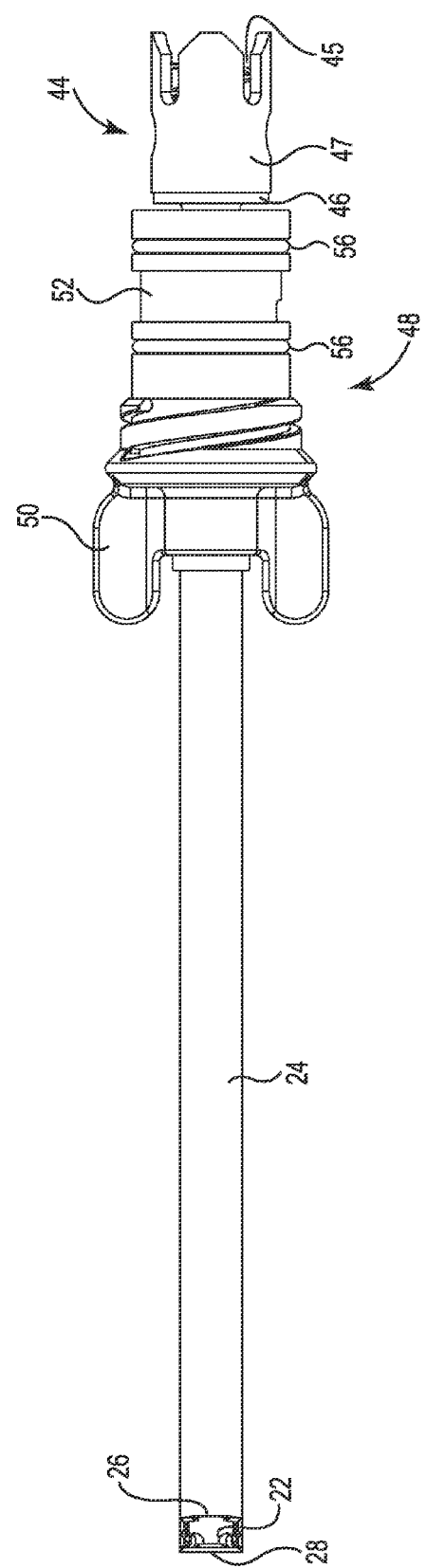
FIGS. 3A and 3B are side and cross-sectional views of a cutting implement of a surgical cutting instrument of FIG. 1.
Figure 3B:
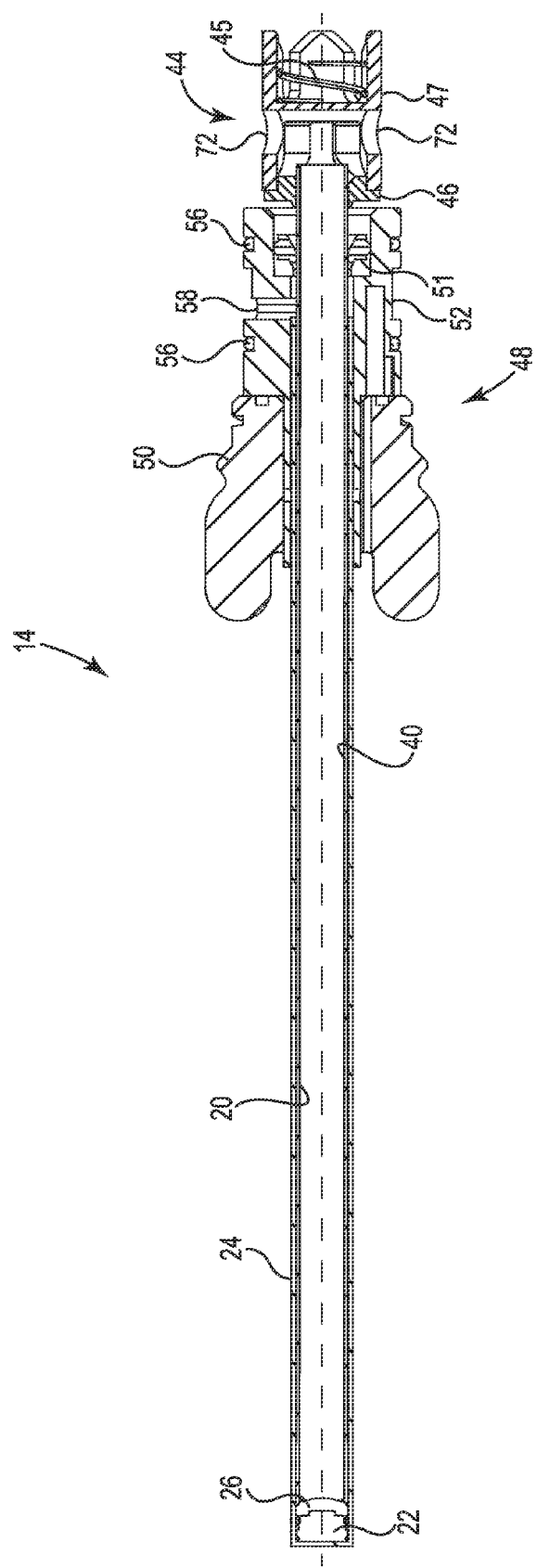

As further illustrated in the cross-sectional view of the cutting implement 14 of FIG. 3B, the inner blade 20 defines an aspiration pathway through an interior of the cutting implement 14 to the cutting tip 22. The inner and outer surfaces of the inner blade 20 are generally smooth and free from burs. The inner blade 20 has a length such that the aspiration pathway may extend continuously through a hub assembly of both the inner blade 20 and the outer blade 24. In particular, the inner blade 20 is coaxially disposed within the outer blade 24 such that a distal end of the outer blade 24 is proximal to a distal end of the inner blade 20. In one embodiment, a proximal end of one or both of the inner and outer blades 20, 24 are textured to include a raised fine diamond knurl or are partially bead blasted (not shown). Regardless, with some constructions, the inner blade 20 is an elongated tubular body and terminates at the distal cutting tip 22.

Figure 6A:
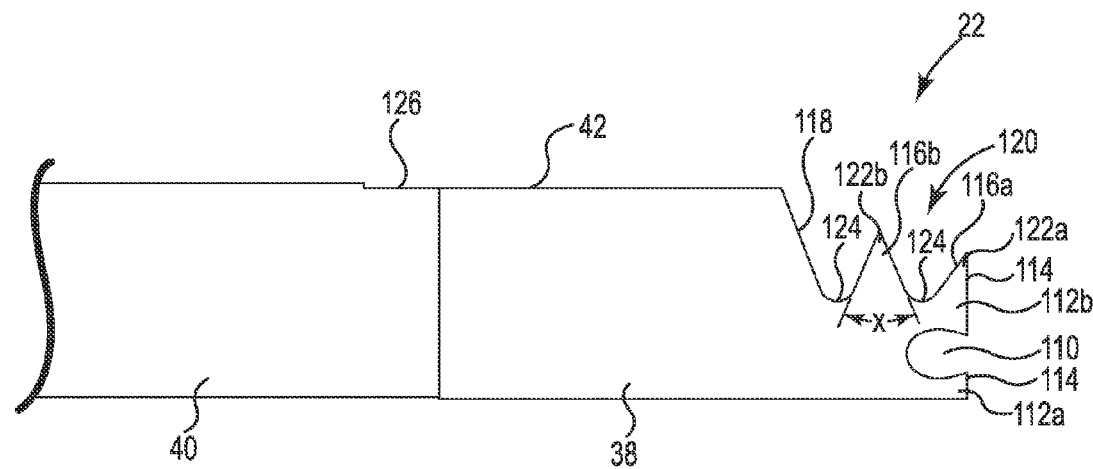
FIGS. 6A and 6B are enlarged side and top views of a distal portion of an inner blade of the cutting implement of FIG. 2.
Figure 6B:
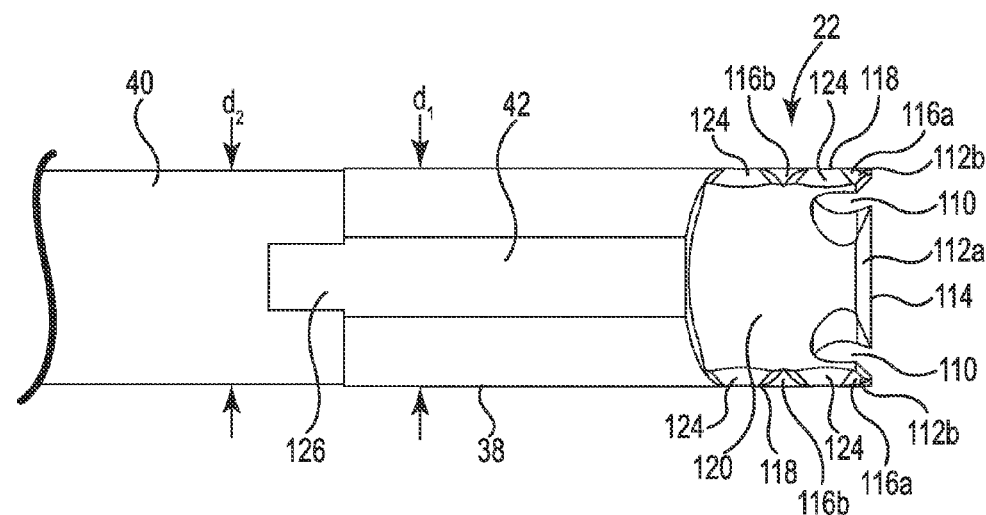

The inner blade 20 defines a lumen between an open proximal end and a distal end, the distal end having an opening therein communicating with a pathway/lumen and forming a suction inlet through which cut bodily tissue can be aspirated. The inner blade 20 has a distal portion 38 and a main portion 40. The cutting tip 22 is formed in the distal portion 38. As best illustrated in FIG. 6B, the distal portion 38 has a first outer diameter $d_1$ slightly larger, or greater, than a second outer diameter $d_2$ of the main portion 40. In one embodiment, the distal portion 38 is laser welded to the main portion 40. An irrigation channel 42 extends from the cutting tip 22 formed on the distal portion 38 and a distal end of the main portion 40. The irrigation pathway extends along the irrigation channel 42 to the cutting tip 22, as described in more detail below.

With continued reference also to FIG. 2, the inner blade assembly 16 includes the inner blade 20 as well as an inner hub assembly 44. As described below, the inner hub assembly 44 maintains the inner blade 20 and facilitates connection of the inner blade assembly 16 to a motor (not shown). The inner hub assembly 44 includes a spring 45, an inner hub 46 and a drive hub 47. The inner hub 46 and the drive hub 47 can assume a variety of forms. The inner hub 46 is adhesively, thermally, or otherwise bonded to the drive hub 47. The inner blade 20 extends to the inner hub 46 and is welded or otherwise bonded to the inner hub 46. The inner blade 20 has an inner surface that defines a lumen. Features associated with one embodiment of the inner hub assembly 44 in accordance with aspects of the present disclosure are shown in greater detail in FIGS. 4A through 4C.

The outer blade 24 is an elongated tubular body defining a central lumen extending between a proximal end and a distal end. With reference to FIG. 3B, when assembled, the inner blade 20 is maintained within the central lumen of the outer blade 24 such that an outer surface of the inner blade 20 and an inner surface of the outer blade 24 define an irrigation pathway to the cutting window 26. The central lumen generally defines uniform inside diameter and is generally uniformly smooth. In one embodiment, an inside diameter of the outer blade 24 is tighter at the distal end of the outer blade 24. For example, in one embodiment, the inside diameter of the outer blade 24 is 0.1465+/−0.001" thru-out except at the distal end having the cutting window 26 where the inside diameter is 0.1465+/−0.0005". The outer blade 24 can be made of tubular members of the differing desired diameters laser welded together. Regardless, the central lumen of the outer blade 24 is sized to accommodate the inner blade 20 coaxially within and maintain the irrigation pathway between walls of the inner blade 20 and outer blade 24.

In addition to the outer blade 24, the outer blade assembly 18 includes an outer hub assembly 48 having a fastener 50, a dynamic seal 51, and an outer hub 52. The outer blade 24 extends distally from within the outer hub 52. The fastener 50 removably secures the hub assemblies 44, 48 within the handpiece 12 (see FIG. 1). The outer hub assembly 48 can assume a wide variety of forms. Features associated with one embodiment of the outer hub assembly 48 in accordance with aspects of the present disclosure are shown in greater detail in FIGS. 5A through 5B.

With reference to FIGS. 3A and 3B, the outer blade 24 is assembled to the outer hub 52 that is in turn coupled to the inner hub 46 of the inner hub assembly 44. The assembled hubs are coaxially received within the handpiece 12 (not shown), with the outer blade 24 and inner blade 20 extending distal the hubs 46, 52 to the distal end 28. The inner hub assembly 44 and the outer hub assembly 48 cooperate to facilitate the rotational relationship of the inner blade 20 and the outer blade 24 by the handpiece 12 that supports both the inner blade assembly 16 and the outer blade assembly 18. Rotation of the inner blade 20 is translated to the cutting tip 22 to effect debulking of the target tissue at the treatment site, as described in greater detail below. With this construction, aspirated liquids and solids (not shown) can be delivered from the cutting tip 22 through the lumen of the inner blade 20 via a sealed pathway. Other constructions capable of effectuating flow of irrigation liquid to the outer blade 24 and aspiration through the inner blade 20 are also envisioned.

Figure 4A:
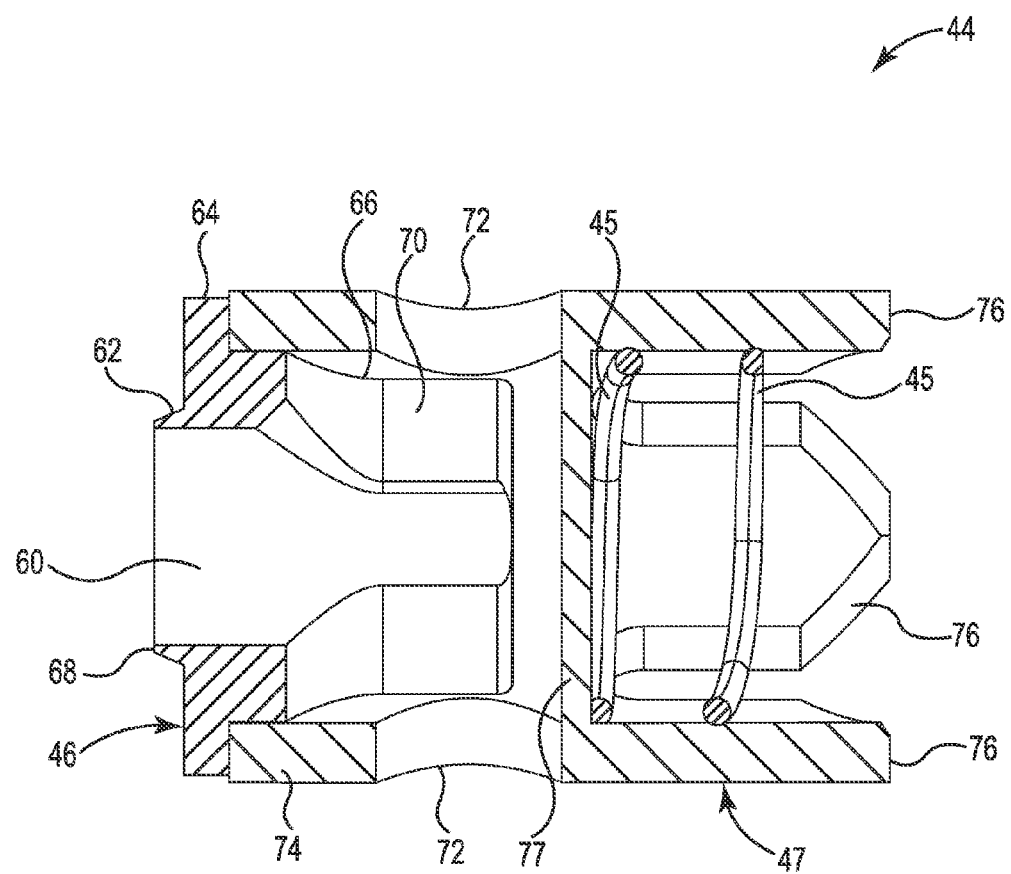
FIGS. 4A through 4C are enlarged cross-sectional and perspective views of an inner hub assembly of the assembly of FIG. 2.
Figure 4B:
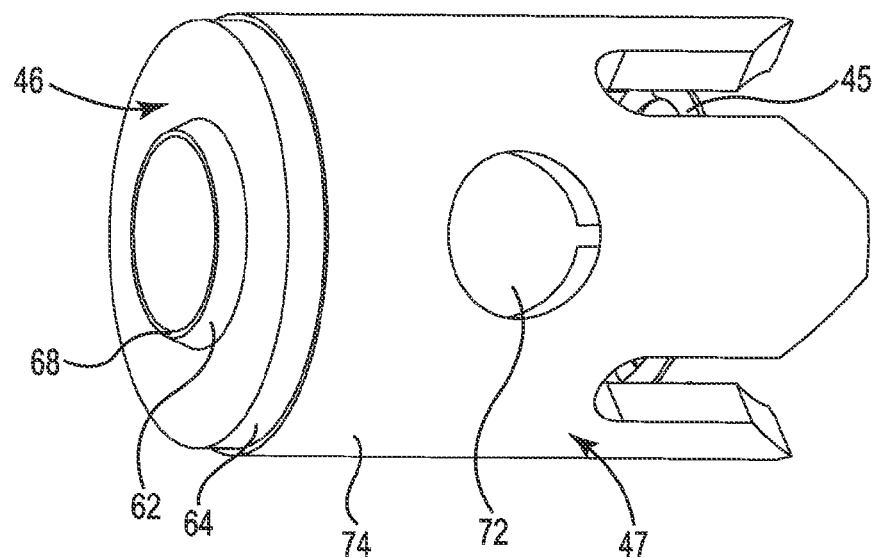
Figure 4C:
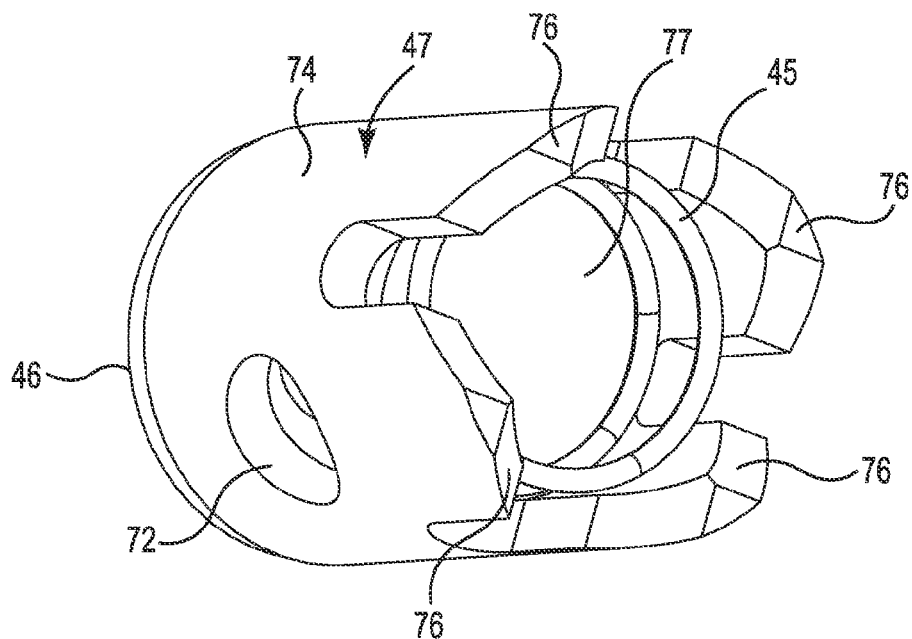

The inner hub assembly 44 is shown in greater detail in FIGS. 4A through 4C and includes the spring 45, the inner hub 46, and the drive hub 47. The inner hub 46 includes a central port 60, a tapered lip 62, a radial flange 64, and walls 66. The central port 60 is sized and shaped to accommodate the inner blade 20. With additional reference to FIGS. 3A and 3B, the inner blade 20 is insertable into and connectable to the inner hub 46 to provide a fluid connection of the interior of the inner blade 20 with the central port 60 of the inner hub 46 along a longitudinal axis (indicated by the dashed line in FIG. 3B). The tapered lip 62 extends from the radial flange 64 to terminate at a rim 68. In one embodiment, the outer surface of the tapered lip 62 extends at a 25° angle from the longitudinal axis (indicated by the dashed line in FIG. 4A) of the central port 60. In one embodiment, the rim 68 of the tapered lip 62 is 0.001" to 0.003" wide around the circumference of the central port 60. In one embodiment, the tapered lip 62 extends 0.010" along the longitudinal axis. Other circumference and height dimensions are also acceptable. The tapered lip 62 effectuates weld joint development between the inner hub 46 and the inner blade 20 (see, e.g., FIG. 3B).

The radial flange 64 extends radially outward from the longitudinal axis greater than the walls 66. As shown in FIG. 4A, in one embodiment, the outer diameter of the radial flange 64 is slightly less than an outer diameter of the drive hub 47. The radial flange 64 abuts the distal end of the drive hub 47 when assembled. The walls 66 extend from a proximal face of the radial flange 64 along the longitudinal axis with an outer diameter that is less than the outer diameter of the radial flange 64. A length of the walls 66 along the longitudinal axis is such that it does not infer with the connection of the drive hub 47 with the motor of the handpiece 12 when assembled. The walls 66 are configured for insertion into the drive hub 47 and have an outer diameter slightly less than an inner diameter of the drive hub 47. The radial flange 64 and the walls 66 sit tightly against the drive hub 47 and form a fluid tight seal. In one embodiment, the walls 66 are tapered slightly inward along all or a proximal portion for ease of insertion into the drive hub 47. The walls 66 include openings 70 that can be configured as slotted openings, oval openings, round openings, or other suitable shape to facilitate fluidly connecting the interior of the inner hub 46, and more particularly the central port 60 of the inner hub 46, with side ports 72 of the drive hub 47. In one embodiment, openings 70 extend and connect linearly across the diameter of the inner hub 46. In one embodiment, the side ports 72 extend perpendicular to the longitudinal axis and the central port 60 and fluidly intersect and are fluidly open to the central port 60.

With further reference to FIGS. 4A through 4C, the drive hub 47 of the inner hub assembly 44 includes perimeter walls 74 terminating at one end in prongs 76. The prongs 76 are configured to facilitate connection with the motor housed in the handpiece 12. The drive hub 47 has an open proximal end and an open distal end. A spring stop 77 extends between the proximal end and the distal end and is generally perpendicular to the perimeter walls 74. The spring stop 77 can be planar and extend to fully separate the spring 45 from the central port 60. The spring stop 77 is formed between the side ports 72 and the prongs 76 on the perimeter walls 74. The spring stop 77 provides a distal stop for springs. The distal end of the drive hub 47 is configured to receive the inner hub 46 and in some cases terminates at a planar surface. The perimeter walls 74 define a cylindrical body. Side ports 72 are formed in the perimeter walls 74. In one embodiment, the perimeter walls 74 include two diametrically opposed side ports 72. The side ports 72 of the drive hub 47 are configured to align and fluidly connect with the openings 70 of the inner hub 46.

Figure 5A:
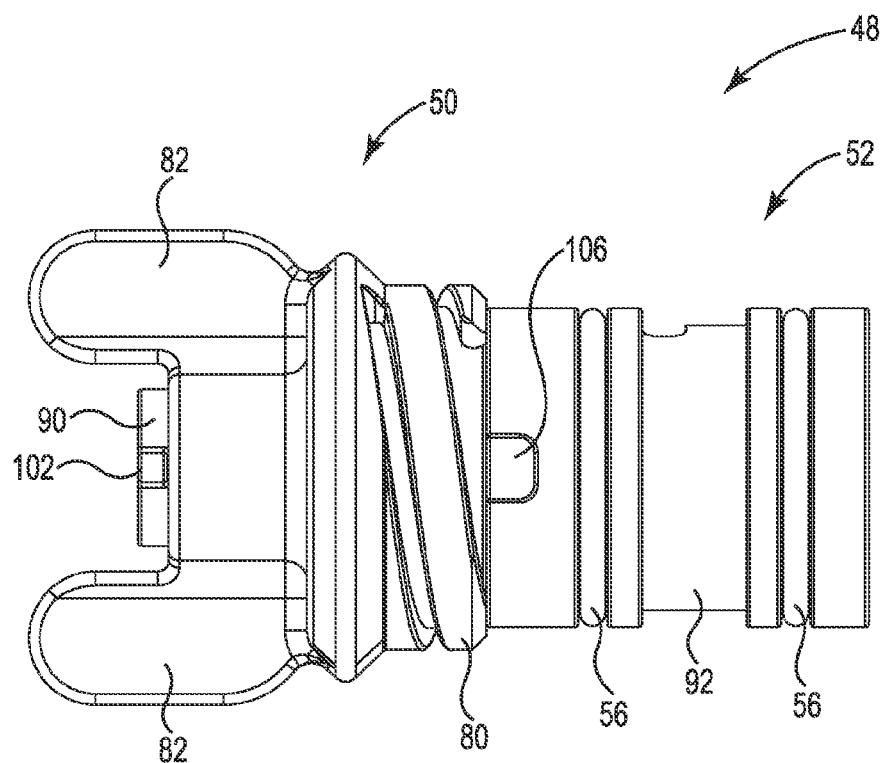
FIGS. 5A and 5B are enlarged side and cross-sectional views of an outer hub assembly of the assembly of FIG. 2.
Figure 5B:
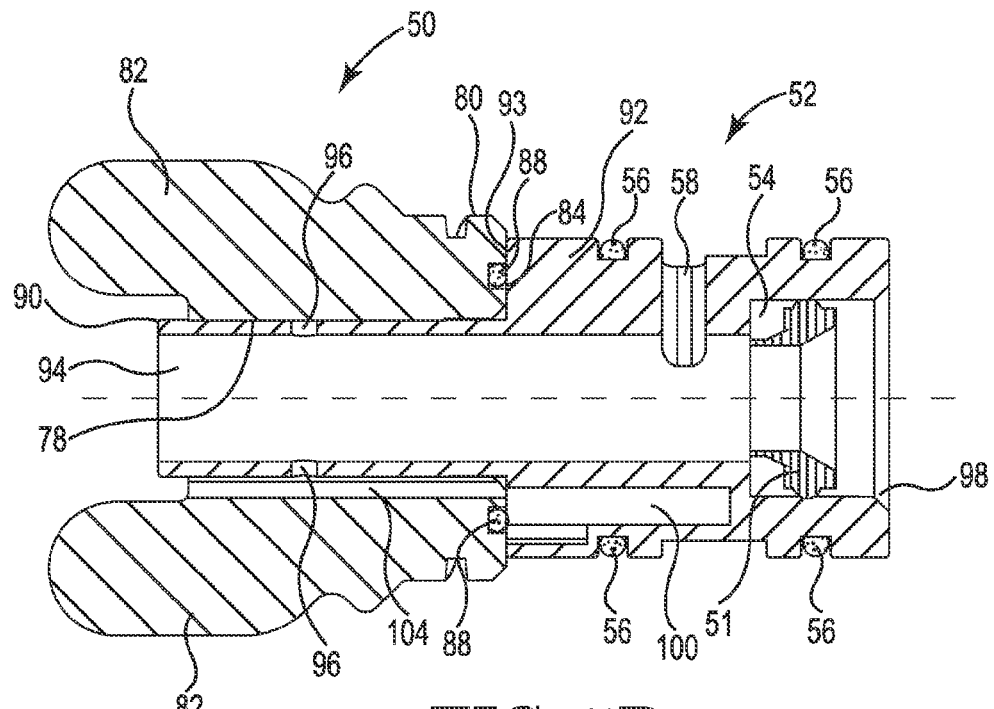

The outer hub assembly 48 is shown in greater detail in FIGS. 5A through 5B and includes the fastener 50 and the outer hub 52. The fastener 50 includes an open core 78 extending longitudinally through the fastener 50 and open at both proximal and distal ends. The core 78 is sized and shaped for a distal portion of the outer hub 52 to extend through, as discussed further below.

The fastener 50 includes threads 80 on an exterior surface to removably secure the outer hub assembly 48 within the handpiece 12 (i.e., threads 80 are mate-able with threads in the handpiece, not shown). The fastener 50 includes winged tabs 82 extending distally away from the threads 80 as well as radially outward. The winged tabs 82 are configured for ease of handling and turning the threads 80 of the fastener 50 to engage or disengage the cutting implement 14 to or from the handpiece 12 (see FIG. 1). Other engagement and disengagement mechanisms are also acceptable. In one embodiment, two winged tabs 82 are included and are disposed on opposing sides of the fastener 50. Other quantities and configurations of winged tabs 82 can also be suitable. In one embodiment, threads 80 are provided to allow the fastener 50 to be turned 180° when securing within the handpiece 12. Sufficient threads 80 are included to prevent the fastener 50 from inadvertently disengaging from the handpiece 12 when the surgical cutting instrument is in use. In any regard, suitable threads 80 are provided to secure the outer hub assembly 48, and the cutting implement 14, to the handpiece 12 until a user rotates the fastener 50 by rotationally pushing against the winged tabs 82 to disengage the threads 80 from the handpiece 12. In one embodiment, a notch 84 is included at a proximal end 86 of the fastener 50. An o-ring 88 is insertable into the notch 84. The o-ring 88 is disposed along the outer hub 52 when assembled and can absorb some of the vibrations of the cutting implement 14 during operation.

The outer hub 52 includes a neck 90 and a base 92. A radial shoulder 93 is defined between the neck 90 and the base 92 and radially extends from an outer diameter of the neck 90 to an outer diameter of the base 92. The neck 90 is sized and configured to extend within and through the fastener 50. A passageway 94 extends through the neck 90 and the base 92. An irrigation port 58 extends from an exterior surface of the outer hub 52 and fluidly connects with the passageway 94. In one embodiment, the passageway 94 extends along the longitudinal axis (indicated by the dashed line in FIG. 5B) and the irrigation port 58 extends perpendicularly to the exterior surface of the outer hub 52. In accordance with aspects of the disclosure, the irrigation port 58 is disposed within the handpiece 12 to fluidly connect to the fluid pathway and irrigation port 32 when assembled to the handpiece 12.

With additional reference to FIG. 3B, the outer blade 24 extends within the passageway 94 and terminates distal to the irrigation port 58 such that the irrigation port 58 freely communicates with the lumen of the outer blade 24. The outer blade 24 is adhesively attached within the outer hub 52. At least one glue weep port 96 extends at an angle to, and in some cases perpendicular, to the longitudinal axis extending along a length of the passageway 94. The at least one adhesive weep port 96 directly and fluidly connects to the passageway 94 and is also fluidly open at an exterior surface of the outer hub 52. Adhesive (not shown), when used to adhere the outer blade 24 within the passageway 94 of the outer hub 52, is inserted in the distal end after or with insertion of the outer blade 24 and excess adhesive can exit the neck 90 at least one adhesive weep port 96 during assembly.

With continued reference to FIGS. 3B and 5B, the inner blade 20 extends beyond the proximal end of the outer blade 24 and through the dynamic seal 51 disposed in a bore 54 at the proximal end portion of the outer hub 52 to connect with the inner hub assembly 44. The dynamic seal 51 fluidly seals around the inner blade 20. In addition, as described in greater detail below, the outer surface of the outer hub 52 is adapted to receive seal rings 56 (e.g., o-rings) on either side of the irrigation port 58 to effectuate a fluid-tight seal between the outer hub 52 and the handpiece 12 (not shown). In some embodiments, the dynamic seal 51 and the seal rings 56 are a polytetrafluoroethylene (PTFE) material such as Teflon®, although other suitable materials are also acceptable.

In one embodiment, as illustrated in FIG. 5B, the proximal end of outer hub 52 includes bevel 98 to provide additional clearance to allow for axial adjustment of the inner hub assembly 44 with respect to the outer hub assembly 48 when adjoined. The bevel 98 of the outer hub 52 enables axial adjustment of the inner hub 46 to allow for seal compression without imparting pre-load to DCM thrust surfaces.

In one embodiment, the outer hub 52 includes an identification port 100. The identification port 100 is configured to accept a radio-frequency identification device (RFID). The RFID includes data to identify the size and blade type, for example, of the cutting implement 14 that is transferred to an integrated power-console (IPC) when the cutting implement 14 is assembled with the handpiece 12. The IPC, upon receiving information from the RFID, can supply power to operate the cutting implement 14 at a suitable speed as well as fluid suitable for the specific cutting implement 14. Other cutting implement identification systems, such as magnetic hall sensors, for example, are also acceptable.

With continued reference to FIGS. 5A and 5B, the outer hub 52 can include a protrusion 102 at the distal end of the neck 90. The protrusion 102 is configured to align with an alignment slot 104 in the fastener 50. The protrusion 102, when rotated and disposed within alignment slot 104, couples the fastener 50 and the outer hub 52 together. Additionally, a tab 106 disposed on the base 92 extends outwardly and is aligned radially with the protrusion 102 on the neck 90. The tab 106 is configured to slidably mate within a slot in a collar of the handpiece 12 (not shown). When assembled, the tab 106 prevents the cutting implement 14 from rotating when in use and provides a reference point to the cutting window 26 orientation.

With reference to FIGS. 5A and 5B, the dynamic seal 51 can be provided to effectuate a fluid-tight seal between the inner blade 20 and the outer blade 24. The dynamic seal 51 can be maintained within the bore 54 at the distal end of the outer hub 52 to seal around the inner blade 20 extending through the outer hub 52. The dynamic seal 51 is configured to fluidly seal around the proximal portion of the inner blade 20. With this construction, an irrigation liquid (not shown) to the outer blade 24 can be delivered to the lumen of the outer blade 24 via a sealed pathway. The inner blade 20 extends through the dynamic seal 51 to fluidly seal within the inner hub 46 of the inner hub assembly 44. With this construction, aspirated liquids and solids (not shown) can be delivered from the cutting tip 22 through the lumen of the inner blade 20 via a sealed pathway. Other constructions capable of effectuating flow of irrigation liquid to the outer blade 24 and aspiration to the inner blade 20 are also envisioned.

Figure 7A:
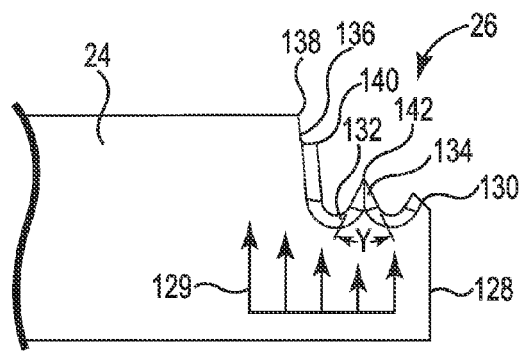
FIG. 7A is an enlarged side view of a distal end of an outer blade of the cutting implement of FIG. 2.
Figure 7B:
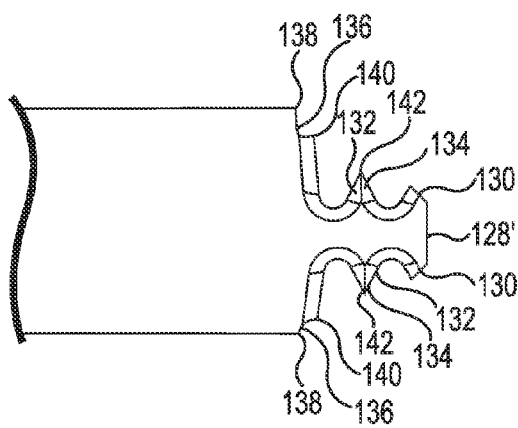
FIG. 7B is an enlarged side view of a distal end of an outer blade of a cutting implement in accordance with principles of the present disclosure.
Figure 7C:
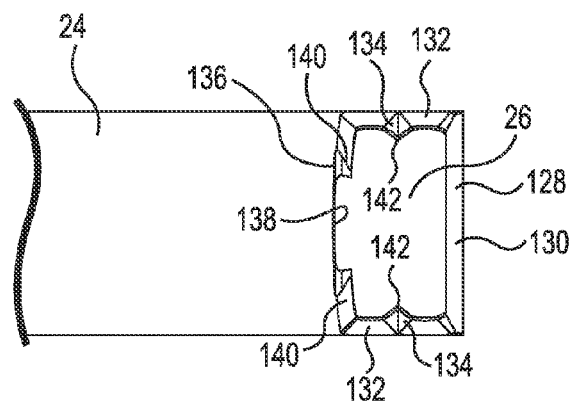
FIG. 7C is an enlarged top view of a distal end of an outer blade of a cutting implement of FIG. 7A in accordance with principles of the present disclosure.

Moving now to the distal end of the inner blade 20, upon final assembly, the cutting tip 22 provided by the inner blade 20 is selectively exposed at the cutting window 26 of the outer blade 24. To this end, FIGS. 6A and 6B provide enlarged side and top views of the distal portion 38 of the inner blade 20 including the cutting tip 22, whereas FIGS. 7A through 7C illustrate embodiments of the distal region of the outer blade 24 including the cutting window 26. Upon final assembly, as best shown in FIGS. 8A and 8B or 9A and 9B, the cutting tip 22 is positioned at the cutting window 26 with the two components begin rotatable relative to one another as discussed above.

The cutting tip 22 includes surfaces or edges for engaging tissue via the cutting window 26 in the distal end of the outer blade 24. The edges of the cutting tip 22 are beveled inwardly to form sharpened cutting edges such that the edge surface are beveled, or angled, toward the interior of the inner blade 20. As the inner blade 20 is rotatably driven at its proximal end, for example by the motorized handpiece 12, the surface or edge of the inner blade 20 will cooperate with the cutting window 26 in the outer blade 24 to shear, cut, or shave the tissue. In general terms, the inner geometry of the cutting tip 22 is designed to impale the tissue as the cutting tip 22 is rotated and provides both end cutting and side cutting via cylindrical geometry. As discussed further below, peripheral edges of the cutting tip 22 opening formed at cutting end of the inner blade 20 are positioned adjacent cutting window 26 such that the cutting edges of the cutting tip 22 can engage bodily tissue through the cutting window 26 and pull the tissue against the edges defining the cutting window 26 to shear the tissue.

With reference to FIGS. 6A and 6B, the cutting tip 22 includes a castellated end having notches 110 that extend between castellations 112a, 112b. In general terms, the castellations 112a, 112b form the distal end cutting surface of the inner blade 20. In one embodiment, a center castellation 112a and opposing side castellations 112b are included with U-shaped notches 110 formed in between the center castellation 112a and each of the side castellations 112b. The distal most end of the cutting tip 22 is defined by end edges 114 formed at a distal end of the castellations 112a, 112b. The end edges 114 are radially planar in a plane perpendicular to the longitudinal axis. The end edges 114 are beveled in a longitudinally inward direction to form a sharpened cutting edge. In one embodiment, the end edges 114 are beveled at a 45° angle.

Teeth 116 on opposing radial side edges 118 of a central opening 120 of the cutting tip 22. The teeth 116 are oriented in opposing pairs that are longitudinally aligned to extend toward each other across the opening 120 of the cutting tip 22 and generally perpendicular to end edges 114 and the castellations 112a, 122b. Edge surfaces of the teeth 116 are beveled, or angled, towards the interior of the inner blade 20. Teeth 116a are formed on the opposing side castellations 112b such that tips 122a are aligned with the end edges 114 and the teeth 116a terminate distally at the end edges 114. At least one pair of teeth 116b is included along the side edges 118 of the central opening 120. The teeth 116a, 116b can have different heights. Valleys 124 are formed between tips 122a and 112b of teeth 116a, 116b. The teeth 116b are formed to have an angle "X".

As discussed above, the first outer diameter $d_1$ of the distal portion 38 is slightly larger, or greater, than the second outer diameter $d_2$ of the main portion 40. For example, in one embodiment, the outer diameter $d_1$ of the distal portion 38 is 0.1452" to 0.1457" and the outer diameter $d_2$ of the main portion 40 is 0.142+/−0.001." In order maintain irrigation flow between the inner blade 20 and the outer blades 24, the irrigation channel 42 is formed along the distal portion 38 of the inner blade 20. In one embodiment, the irrigation channel 42 is a portion of the outer surface that is planar and is recessed to extend within the thickness of the inner blade between the inside surface and the outside surface. The irrigation channel 42 is centered between the side edges 118 to be fluidly open at the central opening 120 of the cutting tip 22. The irrigation channel 42 extends from the central opening 120 of the cutting tip 22, along the distal portion 38, to the main portion 40 of the inner blade 20. The irrigation channel 42 includes a transition section 126 on the main portion 40 adjacent to the distal portion 38. In one embodiment, the distal portion 38 has a length of 0.35" and the irrigation channel 42 has a length of 0.40".

With reference to FIGS. 7A through 7C, the cutting window 26 is formed at the distal end of the outer blade 24 is defined by shearing edges on the tubular sides and an end cap 128 of the outer blade 24. The end cap 128 can be shaped as a segment or a circular zone, for example, at the distal end of the tubular body of the outer blade 24. In this manner, both end cutting and side cutting are provided. The geometry of the cutting window 26 is configured to avoid clogging. For example, the cutting window 26 can have a length equivalent to the inner diameter of the inner blade 20 in order to avoid cutting off pieces of tissue large enough to clog the inner blade 20 and disrupt cutting. The distal end of the outer surface of the outer blade 24 can include markings 129 to visually indicate a depth of the cutting tip 22, and thus the cut, with respect to the tissue. For example, the markings 129 could be placed to indicate a cutting depth of one centimeter, two centimeters, etc. with lines and/or numbers.

In one embodiment, the end cap 128 is planar and the outer blade 24 is cylindrical rather than hemispherical at the distal end. The planar end cap 128 is perpendicular to cylindrical side walls of the outer blade 24. Alternatively, the end cap 128 can be formed as an inverted cone with a center of the inverted cone extending slightly into the interior of the outer blade 24. Regardless, the end cap 128 is joined to the tubular sides of the outer blade 24 to have a squared off interior surfaces along the perimeter. In other words, the interior corners of the distal end of the outer blade 24 at the intersection of the end cap 128 and the tubular side walls of the outer blade 24 are 90° corners. The squared off surfaces expose a maximum surface area to the cutting end edges 114 of the castellations 112a, 112b. Due to the increased cutting surface area, cutting of the tissue occurs more quickly as compared to that of a hemispherical end cutter or a cavitational ultrasonic surgical aspirator (CUSA). For example, in accordance with aspects of the present disclosure, in testing, the cutting implement 14 can resect a chicken breast at 6.78 grams/minute compared to a hemispherical end cutter resection of 2.1 grams/minute and a CUSA at 3.84 grams/minute. As an additional example, during testing the cutting implement 14 in accordance with aspects of the present disclosure can resect a chicken gizzard at 1.88 grams/minute as compared to 1.42 grams/minute with a hemispherical end cutter and 0.82 grams/minute with a CUSA.

The cutting window 26 is defined by outwardly beveled edges. An end window edge 130 is formed on the end cap 128 to form an open semi-circular shape at the distal end 28 of the cutting implement 14. In one embodiment, the end window edge 130 is positioned such that the resulting opening is less than half of the end cap 128. In one embodiment, the end window edge 130 is linear. Side window edges 132 extend from the end window edge 130 along the tubular sides of the outer blade 24. The side window edges 132 are serrated to include window teeth 134. The window teeth 134 are disposed on opposing radial sides of the cutting window 26. Similar to the teeth 116 on the inner blade 20, the window teeth 134 are oriented in opposing pairs that are longitudinally aligned to extend toward each other across the cutting window 26 and extend generally perpendicular to the end cap 128. Edge surfaces of the window teeth 134 are beveled, or angled, towards the exterior of the outer blade 24. A suitable quantity of window teeth 134 are included on the outer blade 24 to correspond with, and interact with, the quantity of teeth 116 on the inner blade 20. In one embodiment, a single pair of window teeth 134 and a single pair of teeth 116b are provided. An angle "Y" formed by the sides of the window teeth 134 complements the angle "X" of the teeth 116b of the inner blade 20. For example, when the angle "Y" of the window teeth is 69° and the angle "X" of the teeth 116b is 59°.

As illustrated in FIG. 7C, the cutting window 26 can be generally rectangular as viewed from the top. A top window edge 136 extends between the side window edges 132 opposite the end window edge 130 to form the cutting window 26. The top window edge 136 includes a center recess 138 and opposing protrusions 140 to form additional shearing surfaces. Unlike the end and side window edges 130, 132, the top window edge 136 extends perpendicularly from the outside surface to the inside surface and is not beveled along the center recess 138.

As illustrated in FIG. 7B, an outer blade 24' can include cutting windows 26 on opposing sides of the outer blade 24'. In one embodiment, two cutting windows 26 are effectively formed on opposing sides of the outer blade 24'. An end cap 128' is formed between the cutting windows 26 as a band, or strip, extending across the end of the outer blade 24' and separating the cutting windows 26 from each other. Aspects of each of the cutting windows 26 of the outer blade 24' are as described above with respect to the cutting window 26 of the outer blade 24.

Figure 8A:
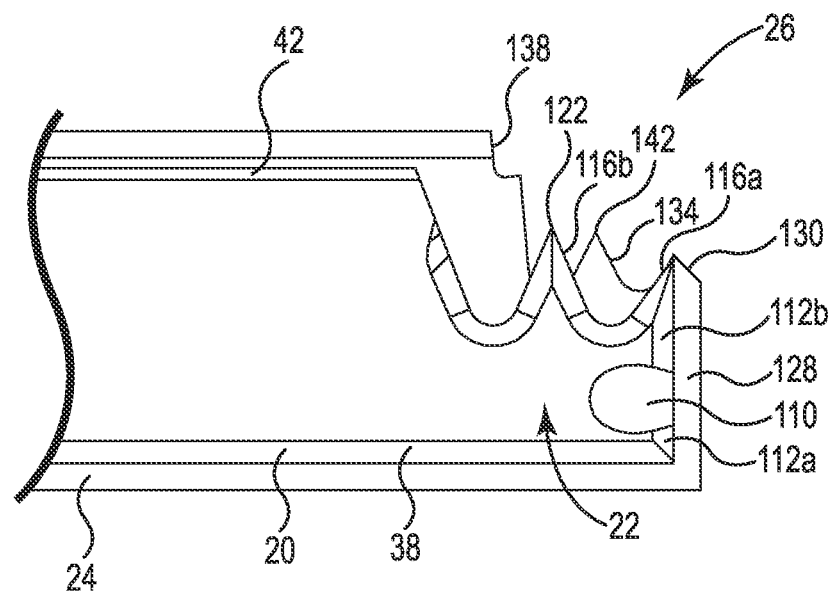
FIGS. 8A and 8B are enlarged cross-sectional and perspective views of an assembled distal end of a cutting implement including the outer blade of FIG. 7A in accordance with principles of the present disclosure.
Figure 8B:
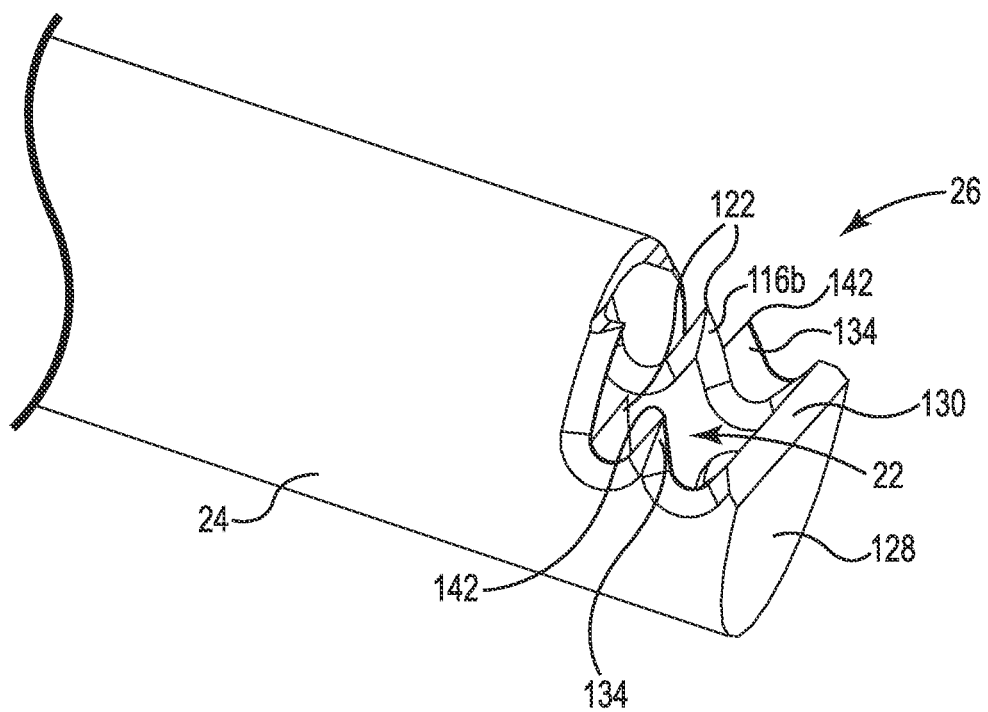
Figure 9A:
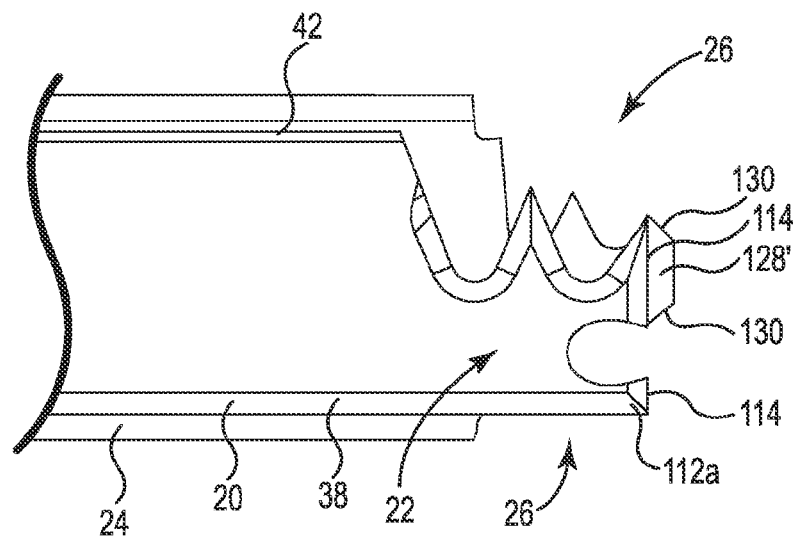
FIGS. 9A and 9B are enlarged cross-sectional and perspective views of an assembled distal end of a cutting implement including the outer blade of FIG. 7B in accordance with principles of the present disclosure.
Figure 9B:
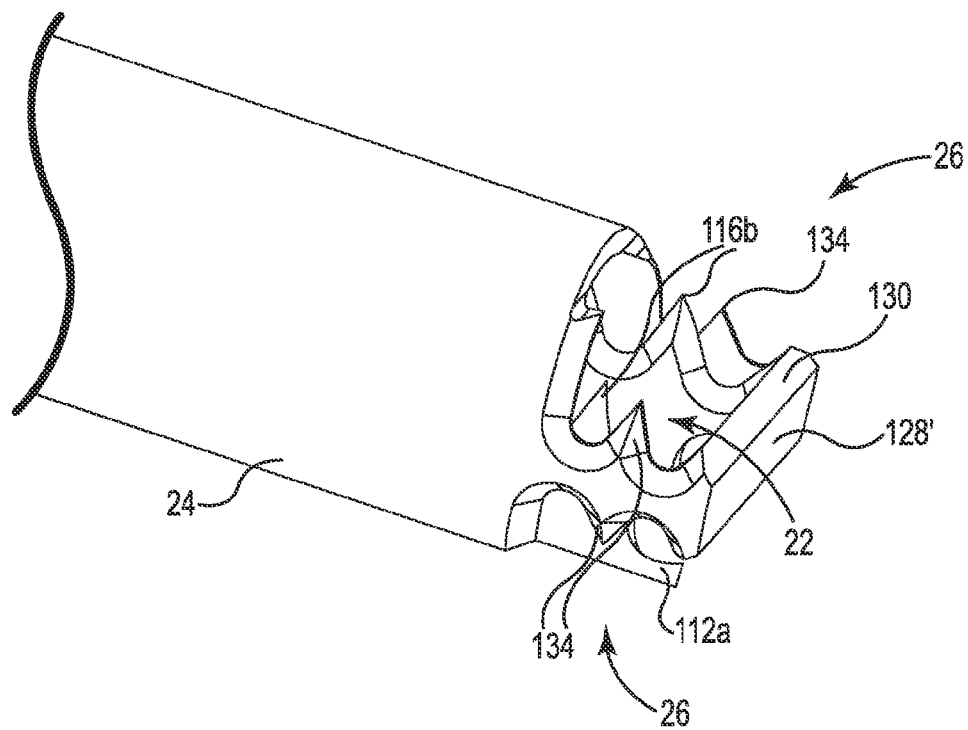

The assembled distal end of a cutting implement 14 including the outer blade 24 of FIG. 7B is illustrated in FIGS. 8A and 8B and the outer blade 24' is included in the assembled distal end illustrated in FIGS. 9A and 9B. In either, as discussed above, the distal portion 38 of the inner blade 20 has a diameter that is larger than the diameter of the main portion 40 of the inner blade 20. The clearance between the outer surface of the distal portion 38 of the inner blade 20 and the inner surface of the outer blade 24 can be 0.0015 inches or less. The outside surface of the inner blade 20 is coated with a biocompatible tungsten-carbide/carbon coating to prevent galling and decrease friction between the inner and outer blades 20, 24. The irrigation channel 42 extends along a length of the inner blade 20 and is fluidly open with the cutting tip 22 in order to maintain irrigation to the cutting tip 22 from between the inner and outer blades 20, 24 and to accommodate the increased diameter of the distal portion 38 of the inner blade 20 within the outer blade 24. With the clearance of 0.0015 inches or less, a shearing of the fibrous tissue between the moving inner blade 20 and the stationary outer blade 24 can occur and tissue is not dragged between the inner and outer blades 20, 24 and eventually torn by multiple rotations of the inner blade 20.

The beveled end edges 114 of the castellations 112a, 112b are configured to directly contact the inner surface the end cap 128 of the outer blade 24 when assembled. The castellated geometry at the distal end of the cutting tip 22 serves to disrupt tissue and drag the tissue toward a low included angle edge on the end cap 128 of the outer blade 24. The end window edge 130 cooperates with the end edges 114 formed on the distal end of the inner blade 20. In use, the distal tips of the castellations 112a, 112b rotationally move against the inside surface of the end cap 128. The castellated geometry provides three hits, or contacts, with the tissue (i.e., one hit per castellation 112a, 112b) during each revolution of the inner blade 20. A spring 45 (see FIGS. 3A and 3B) disposed at the proximal end of the inner blade 20 provides a degree of longitudinal movement for the inner blade 20 with respect to the end cap 128. The spring 45 is biased to extend the inner blade 20 distally toward the end cap 128.

The inner and outer blades 20, 24 can be manufactured of a metal, such as stainless steel, or other hard material suitable for use in surgery. The distal portion 38 of the inner blade 20 is fabricated separately from the main portion 40 and then the distal portion 38 and the main portion 40 are coupled together to form the inner blade 20. The main portion 40 is cut to a desired length from tubing. The distal portion 38 is fabricated from a selected non-tubular material member having a mass such as a cube, a bar, or a rod, for example. The mass of the non-tubular material member is selectively removed to form the desired shape of the distal portion 38. The mass of the non-tubular material member can be selectively removed to form the distal portion 38 using micro-machining such as electrical discharge machining (EDM), mechanical machining, chemical machining, micro-electro-mechanical system (MEMS) processing, or other suitable micro-machining method. A bulk, or majority (greater than 50%), of the mass of the non-tubular material member is removed to create a generally tubular shape and the cutting tip 22 of the distal portion 38. Micro-machining, or other suitable method, can be used to create the profile and the sharp angular beveled edges of the castellations 112a, 112b and the teeth 116a, 116b. The distal portion 38 and the main portion 40 are coupled together via welding or other suitable means. As discussed above, the outer diameter $d_2$ of the main portion 40 is smaller than the outer diameter $d_1$ of the distal portion 38. The irrigation channel 42 is machined, or cut, into the distal portion 38 and the main portion 40 of the inner blade 20. A raised fine diamond knurl can be patterned into the proximal end of the inner blade 20.

The outer blade 24 is manufactured from tubing and plate, or sheet, material. The tubing is cut to a desired length to form the tubular side walls of the outer blade 24. In one embodiment, the sheet material is cut to form two thin planar circular discs concentrically attached together, via welding or other means. The two thin planar discs can have different thicknesses. One of the discs has a diameter corresponding to the inside diameter of the outer blade 24 and fits squarely within the outer blade 24 as the inside surface of the end cap 128. The other disc forming the end cap 128, in this embodiment, has a diameter corresponding to, or is otherwise suitable to be mated with, the outside diameter of the outer blade 24 and forms the outside surface of the end cap 128. The end cap 128 and the tubular side walls of the outer blade 24 are attached together, via welding or other suitable means. The tubular side walls of the tubular member extend along a longitudinal axis and the interior surface of the end cap 128 is perpendicular to the tubular side walls. The interior surface of the tubular side walls intersects squarely with the interior surface of the end cap 128 to form a right angled perimeter. The end cap 128 coupled to the tubular side walls of the outer blade 24 forms squared interior edges at the intersection of the end cap 128 and the tubular sides of the outer blade 24 and avoids the radius that would be created by a boring tool. Alternatively, a single planar disc, or circular plate, can be used to form the end cap 128 having a beveled edge with a smaller and a larger diameter corresponding to the inner and outer diameters of the outer blade 24 to avoid corner radii. Any other method that can create an interior corner without a radius is also acceptable. In one embodiment, the planar disc, or discs, of the end cap 128 are indented in the center to form an inverted conical shape.

The end cap 128 and the tubular walls at the distal end of the outer blade 24 are selectively removed to form the cutting window 26. The outer blade 24 can be micro-machined, or otherwise cut, to form the cutting window 26 with the sharp beveled window edges 130, 132, 136 and window teeth 134. If desired, the markings 129 are etched or otherwise formed into the outer surface of the outer blade 24 at the distal end 28 and a raised fine diamond knurl is patterned into the proximal end of the outer blade 24.

Any burs or weld spatter are removed from the inner and outer blades 20, 24 and the inner and outer blades 20, 24 are flash electro-polished. The inner blade 20 is coupled to the inner hub assembly 44 via welding or other suitable means. The outer blade 24 is coupled to the outer hub assembly 48. The outside surface of the inner blade 20 is coated with a lubricating coating such as a biocompatible tungsten-carbide/carbon coating. The inner blade 20 is inserted into the outer blade 24 such that the cutting tip 22 is positioned to be rotatably exposed at the cutting window 26. The assembled cutting implement 14 is coupled to the handpiece 12 and the fastener 50 is rotated to removably secure the cutting implement 14 to the handpiece 12. Tubing can be coupled to the irrigation and aspiration ports 32, 34 to fluidly connect the surgical cutting instrument 10 to fluid and suction sources.

During use in surgically reducing or removing a tumor or fibrous tissue, the cutting implement 14 is deployed to a target site, with the user manipulating the handpiece 12 to achieve a desired position of the cutting implement 14 relative to the tumor or fibrous tissue. The motor housed within the handpiece 12 effectuates an oscillating tumor cutting operation of the cutting implement 14. Fluid is continuously supplied to the cutting tip 22 by the fluid source via the fluid pathway between the inner and outer blades 20, 24 including along the irrigation channel 42. The aspiration control hole 36 is manually operated by the user to selectively effectuate aspiration at the cutting window 26 generated by a negative pressure source. The aspiration control hole 36 provides the user the ability to vary the rate or level of aspiration at the cutting tip 22 by slidably positioning the user's thumb or finger over an opening of the aspiration control hole 36. Accordingly, when the hole 36 is fully covered, maximum aspiration occurs at the cutting window 26 and when the opening is fully exposed, little or no aspiration occurs. In accordance with aspects of features of this disclosure, degrees of intermediate aspiration at the cutting window 26 can also be achieved.

The sweep of the cutting tip 22 within the cutting window 26 permits cutting when suction is not effective at pulling tissue into the cutting window 26 as can occur with fibrous tissues. The cutting window(s) 26 are open to the aspiration pathway at all times. Suction is used to draw the cut tissue and irrigant from within the cutting window 26 for removal. Suction of the tissue into the cutting window 26 is not required in order to cut the tissue. Fibrous tissue will often not deflect sufficiently under ordinary hospital suction (approximately 300 mm Hg or less). A mixture to irrigant and resected tissue is drawn down the lumen of the inner blade 20 via suction and travels from distal to proximal end and exits out through the handpiece 12.

The sweep of the cutting tip 22 travels through empty space created by the geometry of the cutting window 26. As illustrated in FIGS. 8A-8B and 9A-9B, the teeth 116a, 116b of the inner blade 20 are longitudinally offset from the window teeth 134 of the outer blade 24. More particularly, tips 142 of the window teeth 134 of the cutting window 26 align with the valleys 124 between the teeth 116a, 116b of the cutting tip 22. The teeth 116a, 116b and the castellations 112a, 112b of the cutting tip 22 captures, or affixes, the tissue by locally piercing the target tissue in order to drag the tissue to the stationary window edges 130, 132, and 136 of the cutting window 26 so that a tissue bolus can be sheared free from the in situ fibrous tissue. The inwardly beveled edge surfaces of the cutting tip 22 and the outwardly beveled edge surfaces of the cutting window 26 create sharp shearing surfaces. In this manner, the rotating surface of the cutting tip 22 contacts the target tissue and drives the tissue into the stationary cutting window 26 surfaces to shear the tissue.

Although the present disclosure has been described with reference to preferred embodiments, workers skilled in the art will recognize that changes can be made in form and detail without departing from the spirit and scope of the present disclosure.

What is claimed is:

1. A cutting device for use with a powered surgical tool, comprising:
   an outer blade including a tubular body, an end cap, and a cutting window defined by a beveled edge on the tubular body and the end cap; and
   an inner blade including a cutting tip, the inner blade co-axially disposed within the outer blade such that the cutting tip is rotatably exposed at the cutting window, the cutting tip having castellations, opposing teeth, a first opening, and a second opening, wherein the second opening is circumferentially spaced from the first opening at a distal most end of the inner blade, wherein the castellations extend parallel to a longitudinal axis of the inner blade toward the end cap of the outer blade between the first opening and the second opening, and wherein the opposing teeth extend radially toward one another across the first opening of the cutting tip and generally perpendicular to the castellations.

2. The cutting device of claim 1, wherein an interior surface of the end cap is formed at a right angle to an inner surface of the tubular body of the outer blade.

3. The cutting device of claim 1, wherein the beveled edge of the cutting window is beveled in an outward direction.

4. The cutting device of claim 1, wherein the castellations and the teeth of cutting tip are beveled in an inward direction.

5. The cutting device of claim 1, wherein the cutting window includes window teeth on opposing sides.

6. The cutting device of claim 5, wherein the window teeth of the cutting window are offset from the teeth of the cutting tip along a longitudinal axis.

7. The cutting device of claim 1, wherein the cutting window includes a semi-circular opening at the end cap.

8. A cutting device for use with a powered surgical tool, comprising:
   an outer blade having a distal end having an end cap, wherein the end cap is planar and perpendicular to cylindrical sides of the outer blade, wherein a distal cutting window is formed in the end cap and the cylindrical sides, and wherein the distal cutting window is defined by edges having protrusions and window teeth; and
   an inner blade having a distal portion including a cutting tip, wherein the cutting tip includes teeth configured in pairs that extend radially toward one another across a first opening and castellations that extend parallel to a longitudinal axis of the inner blade toward the end cap of the outer blade, wherein the castellations extend along the distal portion between the first opening and a second opening, and wherein the second opening is circumferentially spaced from the first opening;
   wherein the inner blade is disposed coaxially within the outer blade along a longitudinal axis with the cutting tip aligned within the cutting window, and
   wherein the window teeth of the cutting window are longitudinally offset from the teeth of the cutting tip.

9. The cutting device of claim 8, wherein the distal portion of the inner blade has a first outer diameter and a proximal portion of the inner blade has a second outer diameter, wherein the first outer diameter is greater than the second outer diameter.

10. The cutting device of claim 9, wherein the distal portion includes an irrigation channel recessed from the first outer diameter, and a transition length of the proximal portion has a transition section adjacent the distal portion, the transition section having a length less than a length of the distal portion.

11. The cutting device of claim 8, further comprising an inner hub assembly including a spring, wherein proximal an end of the inner blade is coupled to the inner hub assembly, and wherein the spring is configured to bias the inner blade distally when the inner hub assembly is assembled to a surgical handpiece.

12. The cutting device of claim 11, further comprising an outer hub assembly including a dynamic seal, wherein the inner and outer blades extend within the outer hub assembly, and wherein the inner blade extends proximally through the dynamic seal to the inner hub assembly.

13. The cutting device of claim 8, wherein the castellations extend toward and contact an inner surface of the end cap of the outer blade.

14. The cutting device of claim 8, wherein the castellations have end edges beveled at 45°.

15. The cutting device of claim 8, wherein the castellations include a center castellation disposed opposite the first opening and side castellations disposed on each side of the center castellation, and wherein the second opening includes U-shaped notches formed between the center castellation and each of the side castellations.

16. The cutting device of claim 8, wherein the outer blade includes a second distal cutting window radially opposed to the distal cutting window.

\* \* \* \* \*